US010355512B2

(12) United States Patent
Cinbis et al.

(10) Patent No.: US 10,355,512 B2
(45) Date of Patent: Jul. 16, 2019

(54) FOCUSED POWER TRANSFER FOR IMPLANTABLE MEDICAL DEVICE

(71) Applicant: Medtronic, Inc., Minneapolis, MN (US)

(72) Inventors: Can Cinbis, Salt Lake City, UT (US); Richard J O'Brien, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 210 days.

(21) Appl. No.: 15/212,605

(22) Filed: Jul. 18, 2016

(65) Prior Publication Data
US 2017/0025888 A1    Jan. 26, 2017

Related U.S. Application Data

(60) Provisional application No. 62/195,843, filed on Jul. 23, 2015.

(51) Int. Cl.
*A61N 1/37* (2006.01)
*H02J 7/02* (2016.01)
(Continued)

(52) U.S. Cl.
CPC ........... *H02J 7/025* (2013.01); *A61B 5/0031* (2013.01); *A61B 5/0205* (2013.01); *A61B 5/686* (2013.01);
(Continued)

(58) Field of Classification Search
CPC ...... H02J 7/025; H02J 50/10; A61N 1/37223; A61N 1/37229; A61N 1/3787; H04B 5/0037; A61B 2560/0219
See application file for complete search history.

(56) References Cited

U.S. PATENT DOCUMENTS

| 8,003,965 B2 * | 8/2011 | Grbic | B82Y 20/00 250/505.1 |
| 8,216,134 B2 | 7/2012 | Ries et al. | |

(Continued)

FOREIGN PATENT DOCUMENTS

| WO | 2008/144677 A1 | 11/2008 |
| WO | 2012/126003 A1 | 9/2012 |

OTHER PUBLICATIONS

(PCT/US2016/042875) PCT Notification of Transmittal of the International Search Report and the Written Opinion of the International Searching Authority, dated Sep. 23, 2016, 12 pages.
(Continued)

*Primary Examiner* — Eric D. Bertram (57) ABSTRACT

A rechargeable cell of an implantable medical device is recharged by an external charging unit that includes a transmitting coil configured to emit an electromagnetic field and a near-field focusing plate having a subwavelength structure pattern that focuses the emitted electromagnetic field to a focal pattern. The implantable medical device includes a housing having a window of an electromagnetically transparent material and a receiving coil enclosed by the housing. The receiving coil extends adjacent to and is aligned with the window. The rechargeable cell is enclosed by the housing and is configured to be charged by current induced in the receiving coil when the receiving coil is exposed to the focal pattern. In some examples, the near-field focusing plate is configured to produce the focal pattern to have a size that is less than an outer dimension of the window and a focal length from the near-field focusing plate that at least reaches the window.

14 Claims, 3 Drawing Sheets

(51) Int. Cl.
　　　*H02J 50/80*　　　(2016.01)
　　　*H02J 50/10*　　　(2016.01)
　　　*A61B 5/00*　　　(2006.01)
　　　*A61B 5/0205*　　(2006.01)
　　　*A61N 1/372*　　　(2006.01)
　　　*A61N 1/378*　　　(2006.01)
　　　*H04B 5/00*　　　(2006.01)
　　　*H02J 50/12*　　　(2016.01)
　　　*A61N 1/375*　　　(2006.01)
　　　*A61B 5/04*　　　(2006.01)

(52) U.S. Cl.
　　　CPC ....... *A61N 1/3787* (2013.01); *A61N 1/37223* (2013.01); *A61N 1/37229* (2013.01); *H02J 50/10* (2016.02); *H02J 50/12* (2016.02); *H02J 50/80* (2016.02); *H04B 5/0037* (2013.01); *H04B 5/0093* (2013.01); *A61B 5/04* (2013.01); *A61B 2560/0219* (2013.01); *A61N 1/3758* (2013.01)

(56) References Cited

U.S. PATENT DOCUMENTS

| | | | |
|---|---|---|---|
| 8,593,107 | B2 | 11/2013 | Penner et al. |
| 8,849,402 | B2 | 9/2014 | Bohori et al. |
| 2004/0147973 | A1 | 7/2004 | Hauser |
| 2012/0119698 | A1* | 5/2012 | Karalis ................ B60L 11/182 320/108 |
| 2014/0094674 | A1 | 4/2014 | Nurmikko et al. |
| 2015/0321011 | A1 | 11/2015 | Carney et al. |
| 2015/0321012 | A1 | 11/2015 | Cinbis et al. |
| 2015/0321016 | A1 | 11/2015 | O'Brien et al. |
| 2016/0087458 | A1 | 3/2016 | Grbic et al. |

OTHER PUBLICATIONS

Ho et al., "Wireless power transfer to deep-tissue microimplants", PNAS, Jun. 3, 2014, vol. 111, No. 22, pp. 7974-7979.

\* cited by examiner

FOCUSED POWER TRANSFER FOR IMPLANTABLE MEDICAL DEVICE

CROSS-REFERENCE TO RELATED APPLICATIONS

This application claims the benefit of U.S. Provisional Application No. 62/195,843 filed on Jul. 23, 2015. The disclosure of the above application is incorporated herein by reference in its entirety.

TECHNICAL FIELD

The disclosure relates to implantable medical devices and apparatus and methods for focused power transfer for recharging an energy storage device of the implantable medical device from an external power source.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to and/or monitor conditions of a variety of organs, nerves, muscle or tissue, such as the heart, brain, stomach, spinal cord, pelvic floor, or the like.

In order to promote patient comfort, IMDs are often miniaturized. In some cases, IMDs are miniaturized in order to be implantable at a desired anatomical site or enable minimally invasive implant procedures to be used. Available space within an IMD housing for a power supply that powers IMD electronic circuitry is therefore limited. Depending on the particular medical application, an IMD may be required to function for weeks, months or even years, sometimes continuously. The power supply can become depleted requiring IMD replacement.

DETAILED DESCRIPTION

Figure 1:
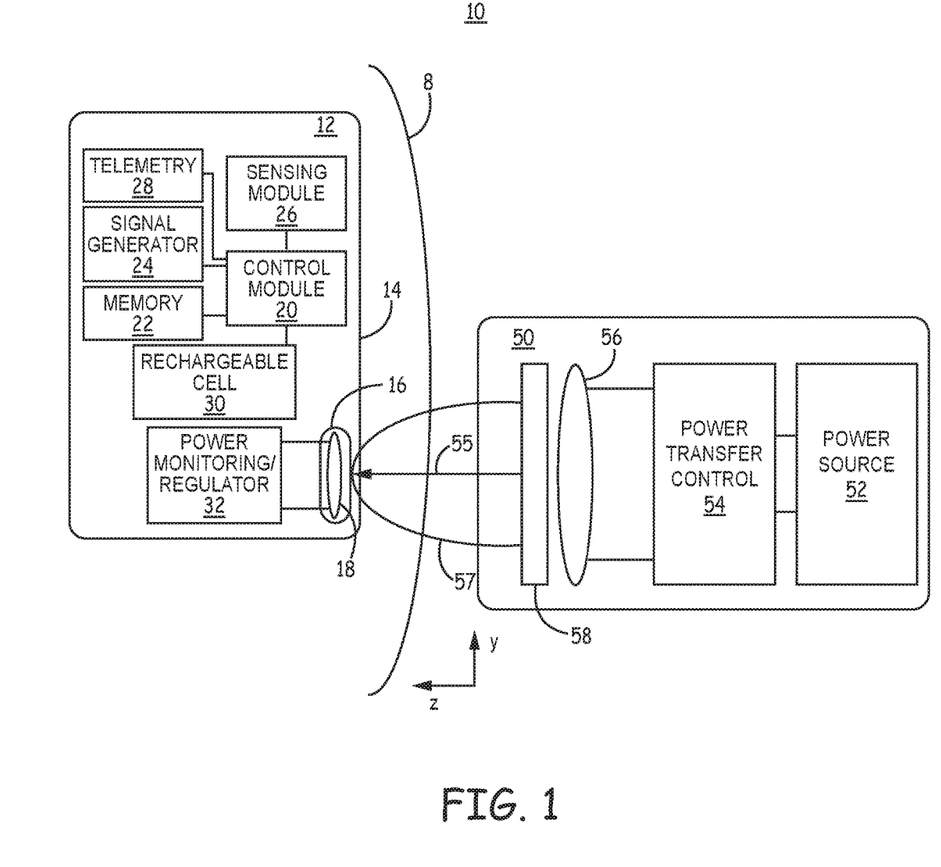
FIG. 1 is a conceptual diagram illustrating a rechargeable IMD system according to one example.

FIG. 1 is a conceptual diagram illustrating a rechargeable IMD system 10 according to one example. IMD system 10 includes IMD 12 and an external charging unit 50. IMD 12 is implantable beneath a patient's skin 8 and may be positioned in a subcutaneous, subfascial or submuscular location. In other examples, IMD 12 may be implanted within the cranium, thoracic cavity, abdominal cavity, an organ such as within the brain, digestive system, the heart, blood vessels, or any other internal body location. IMD 12 includes a hermetically sealed housing 14 that encloses and protects IMD electronic circuitry from body fluids.

IMD 12 may be configured as a monitoring device that senses one or more physiological signals, e.g., a cardiac monitor sensing cardiac electrical signals, blood pressure signals, heart sounds, oxygen saturation or other physiological signals. Other types of monitors may include a respiration monitor, a blood chemistry monitor (such as an insulin monitor), or an electrophysiological monitor. As such, IMD 12 may include a sensing module 26 that is coupled to one or more sensors. Sensors coupled to IMD 12 and sensing module 26 may include one or more electrodes carried by the housing 14 of IMD 12, one or more electrodes carried by a medical electrical lead coupled to IMD 12, and/or one or more electrodes carried by an insulated, electrically conductive extension extending from IMD housing 14. In other examples, sensors coupled to sensing module 26 may include a pressure sensor, optical sensor, acoustical sensor, motion sensor, or other sensor used with IMDs for sensing physiological signals for monitoring a condition or state of a patient.

IMD 12 may additionally or alternatively be configured to deliver an automatic therapy. For example, IMD 12 may be a cardiac pacemaker or neurostimulator configured to deliver therapeutic electrical stimulation pulses. As such, IMD 12 may include a signal generator 24 that is coupled to a pair of electrodes for delivering electrical stimulation pulses. As indicated above, a pair of electrodes may be carried by IMD housing 14, by a medical electrical lead and/or by an insulated, electrically conductive extension extending from housing 14.

IMD 12 may include a control module 20 that controls IMD functions, such as sensing and/or therapy delivery functions. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. The functions attributed to IMD 12 may be embodied as one or more processors, controllers, hardware, firmware, software, or any combination thereof. The functional operation of IMD system 10 as disclosed herein should not be construed as reflective of a specific form of software or hardware necessary to practice the methods described. Providing software, hardware, and/or firmware to accomplish the described functionality in the context of any modern IMD system, given the disclosure herein, is within the abilities of one of skill in the art.

Memory 22 may store control parameters and algorithms used by control module 20. Memory 22 may include computer-readable instructions that, when executed by control module 20 cause IMD 12 to perform various functions attributed throughout this disclosure IMD 12. The computer-readable instructions may be encoded within memory 22. Memory 22 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

IMD 12 may include a telemetry module 28 capable of wireless, radiofrequency communication with an external device for sending and receiving data. Data transmitted to IMD 12 may include programming commands and operating control parameters. Data transmitted from IMD 12 may include data acquired by IMD 12, including physiological signal data and/or data relating to the operation and performance of IMD 12.

IMD housing 14, which encloses the various modules described above, is formed of a biocompatible material and may be a metallic housing such as a stainless steel or titanium alloy. In some examples, at least a portion of housing 14 is an electrically conductive metal and may be used as an electrical ground connection and in some cases as an electrode coupled to signal generator 24 and/or sensing module 26.

IMD 12 includes a power source that includes at least one rechargeable cell 30 for powering the various modules described above. In some examples, IMD 12 is powered solely from rechargeable cell 30 and in other examples a non-rechargeable primary cell (not shown) may be included in addition to the rechargeable cell 30 shown in FIG. 12. By including a rechargeable cell 30, the functional life of IMD 12 may be extended by transmitting power to IMD 12 for recharging cell 30 as needed. The overall size of IMD 12 may be reduced by including rechargeable cell 30 for providing at least a portion of the IMD 12 power requirements. A primary cell to power IMD 12 for the duration of the desired functional life of IMD 12 can be significantly reduced in size or eliminated by including rechargeable cell 30.

When housing 14 includes a metallic, electrically conductive material, at least a portion of housing 14 is formed of an electromagnetically transparent material for promoting efficient power transmission to a receiving coil 18 enclosed within housing 14. In the example shown, housing 14 includes an electromagnetically transparent window 16 extending over an internal, receiving coil 18 enclosed by housing 14. Window 16 may be a discrete window that is assembled within an opening of a metallic housing 14, for example using a ferrule and brazing techniques or other bonding or sealing methods to form a hermetic seal between window 16 and the metallic housing 14.

External charging unit 50 includes a power source 52, power transfer control 54, transmitting coil 56, and near-field focusing plate 58. Power source 52 may be an AC power source, a primary battery, or a rechargeable battery. Power transfer control 54 is configured to convert a power supply signal from power source 52 to a drive signal applied to transmitting coil 56. Transmitting coil 56 may be a single turn coil or include multiple turns and can also be made of multiple coils for impedance matching purposes for optimizing power transfer.

The drive signal applied to transmitting coil 56 may have a frequency of up to 16 MHz to keep tissue losses negligible, with no limitation intended, and produces an electromagnetic field that is focused by near-field focusing plate 58. Near-field focusing plate 58 includes focusing structures, e.g., linear structures or azimuthal structures that may be micromachined or printed structures. The focusing structures may include combination of capacitive and/or inductive elements that collectively provide a surface reactance of the near-field focusing plate that produces a subwavelength focal pattern. The focusing structures of near-field plate 58 converge the electromagnetic field lines induced by the drive signal applied to coil 56 to a linear or spot focal pattern in a focal plane at the target receiving coil 18.

Near-field inductive power transmission without near-field focusing plate 58 is inefficient due to the inherent exponential decay of the EM energy in the near-field which is mostly magnetic. When near-field focusing plate 58 is not used, the receiving coil may be required to be similar in size to the transmit coil in order to provide effective coupling and their respective sizes need to be proportional to the distance between them. By utilizing near-field focusing plate 58, the focusing structures provide sub-wavelength focus of the induced EM field 57 beyond the diffraction limit, allowing the receiving coil 18 to be significantly reduced in size relative to the transmitting coil 56 and overcoming the inherent exponential decay of the EM field. Efficient power transfer is achieved in the near-field while reducing the size of the receiving coil 18, and thus overall size of IMD 12 and/or increasing available space for other IMD components. For example, the receiving coil 18 may have an outer diameter that is 1 cm or less.

The near-field focusing plate 58 may be fabricated using micromachining, lithography or other techniques for creating sub-wavelength near-field focusing of the EM field generated by transmitting coil 56. Example methods for designing planar sub-wavelength patterned structures to provide near-field EM focusing beyond the diffraction limit based on a desired focal pattern of the EM field are generally disclosed in U.S. Pat. No. 8,003,965 (Grbic, et al.), incorporated herein by reference in its entirety. The focusing structures of near-field focusing plate 58 are selected to provide a desired spot size or linear focal pattern within the bounds of the window 16 to provide efficient EM coupling to receiving coil 18.

To improve coupling between the transmitting coil 56 and receiving coil 18, window 16 is provided as an electromagnetically transparent window to minimize dispersion and attenuation of the focused subwavelength field. When IMD housing 14 is formed of a metal, window 16 minimizes heating losses and attenuation by housing 14. Window 16 has an outer dimension 48 defined by a length or width (or diameter when window 16 is generally circular) that is at least as large as the focal pattern size of the focused EM field 57 at coil 18. In an illustrative example, the focal pattern produced by near-field focusing plate 58 is a spot that is less than 1 cm in diameter. Window 18 has an outer dimension 48 that is at least 10% greater than the spot size but may be less than 50% greater than the intended focal pattern size. The focusing structures of near-field focusing plate 58 are selected to produce focal pattern size in a focal plane at coil 18 such that at least 90% of the near-field magnetic flux passes through the window 16. The receiving coil 18 and window 16 may be generally circular, and coil 18 may have an inner diameter that is equal to or greater than the diameter of window 16.

Near-field focusing plate 58 may be a passive plate designed to have capacitive and inductive structures for focusing the near-field magnetic flux at the receiving coil 18. In other examples, near-field focusing plate 58 is an actively controlled plate that is electronically controlled by power transfer control 54 to select the active structures of the near-field focusing plate 58 thereby altering the focal pattern and/or focal length 55. In some cases, near-field focusing plate 58 is a multi-layer near-field plate in which layers are selectable by power transfer control 54 to provide a desired focus pattern. An actively controlled near-field focusing plate 58 may be controlled to adjust the EM field 57 in the x-, y- and/or z-directions to control the focal length 55 (z-direction) and the lateral position (y-direction) and/or longitudinal position (x-direction, into the paper) of the focal spot (or line) so that the focal pattern is maintained in a focal plane that exposes receiving coil 18 to the focused EM field 57. Control of the focal length and transverse location of the focal pattern may enable focusing of EM field 57 on the receiving coil 18 through window 16 when IMD 12 is subjected to motion, e.g., of a beating heart or respiration. Control of the focal length and pattern may also be used to compensate for displacement or motion of the transmitting coil 56 with respect to the IMD 12. For example, the transmitting coil 56 may be mounted in a wearable vest to enable ambulatory charging of the IMD 12.

In other examples, transmitting coil 56 is an array of transmitting coils which may be focused by near-field focusing plate 58 implemented as a single passive focusing plate, multiple passive focusing plates, or an actively controlled near-field focusing plate. One or more transmitting coils of the array of coils may be selected for power transmission to direct the EGM field 57 toward the targeted receiving coil 18. In other cases, multiple coils of a coil array of transmitting coil 56 that are aimed in different directions may be activated to transmit power so that at least one or more become actively coupled with receiving coil 18.

In some examples, the EM field 57 is used as a triggering signal to cause IMD 12 to deliver therapy by signal generator 24 and/or enable monitoring of a physiological signal by sensing module 26. Power monitoring/regulator may provide a trigger signal directly to control module 20, signal generator 24 or sensing module 26 when current is induced on receiving coil 18 by EM field 57. The trigger signal enables or turns "on" therapy delivery and/or sensing functions performed by signal generator 24 or sensing module 26, respectively.

The signal generator 24 may respond to the trigger signal by delivering a therapeutic electrical stimulation pulse. The trigger signal may be a control signal that causes the signal generator 24 to deliver a pulse that is powered by rechargeable cell 30. For example, upon receiving the trigger signal from power monitoring/regulator 32, rechargeable cell 30 (or a non-rechargeable primary power source) may be used to charge capacitors included in signal generator 24 to a desired voltage that is discharged through a therapeutic load in response to receiving the trigger signal.

In other examples, the trigger signal provides both the signal to deliver an electrical stimulation pulse as well as the power for charging one or more capacitors included in signal generator 24 to a desired voltage that is discharge through a therapeutic load, e.g., through electrodes coupled to signal generator 24. In this way, IMD 12 may function as a "passive" therapy delivery device that is effectively a conduit for transferring energy received from external charging unit 50 to a therapy delivery site. A rechargeable cell 30 may be optional in this case and a potential developed by the induced current may be coupled directly to signal generator 24 by power monitoring and regulator 32, e.g., for charging capacitors to a programmed therapy delivery voltage, without an intervening energy storage cell. External charging unit 50 controls provides both the timing of the stimulation pulse (i.e., when EM field 57 is produced) and the power for delivering the stimulation pulse via power transfer from external charging unit 50.

The sensing module 26 may respond to the trigger signal by enabling transducers, sense amplifiers, digital convertors and/or other sensing module components to receive a physiological signal and pass the physiological signal (or event marker signals corresponding to the time that physiological events are sensed from the physiological signal) to control module 20, memory 22, and/or telemetry module 28. Sensing module 26 may be configured to acquire a physiological signal as long as EM field 57 is present and inducing current in receiving coil 18.

In some examples, the current induced in receiving coil 18 while EM field 57 is present provides the power required by sensing module 26 for the duration of the physiological signal monitoring. In this way, IMD 12 may operate as a "passive" sensor in that the time that the sensing module 26 is operating to acquire a physiological signal is controlled by the presence of EM field 57 and the power required to obtain the physiological signal for the duration of a monitoring interval is provided by the presence of EM field 57. In other words, sensing module may only function to acquire a physiological signal when EM field 57 is present.

Alternatively, sensing module 26 may be triggered to start a monitoring function in response to a trigger signal from power monitoring/regulator 32 when current is induced in coil 18 and then execute the monitoring function according to a predetermined protocol regardless of how long EM field 57 is present. Rechargeable cell 30 (and/or another non-rechargeable power source) may power the physiological signal sensing functions performed by sensing module 26.

In other examples, power transfer from external charging unit 50 may provide a "wake up" signal to telemetry module 28. Power monitoring/regulator 32 may respond to a current signal induced in receiving coil 18 by passing a signal to telemetry module 28 that powers up a transceiver for sending and receiving wireless telemetry signals with another IMD (not shown) or an external device, e.g., an external programmer, home monitor or handheld device. Telemetry module may remain powered up and enabled for bidirectional communication with another device as long as EM field 57 is present and focused on receiving coil 18 (via window 16) or may remain powered up by rechargeable cell 30 (and/or another non-rechargeable power source) as long as the communication session with another device is active.

In each of these examples in which the presence of the focused near-field EM energy is used to signal a component of IMD 12 to perform a function (which may be in addition to providing the power required to perform the function), power monitoring/regulator 32 may include a high impedance load that enables a potential to be generated for providing a trigger signal with a very low current bias or no bias at all. In this way, a very low- or zero-power wake-up or operation trigger of IMD 12 is achieved when the trigger signal is generated by power monitoring/regulator 32 in response to the focused near-field EM energy producing a focal pattern at focal length 55.

Figure 2A:
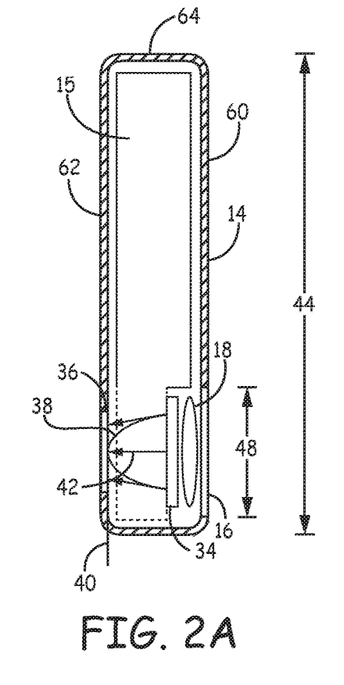
FIG. 2A is side view and FIG. 2B is a back view of conceptual diagram of an IMD according to another example.
Figure 2B:
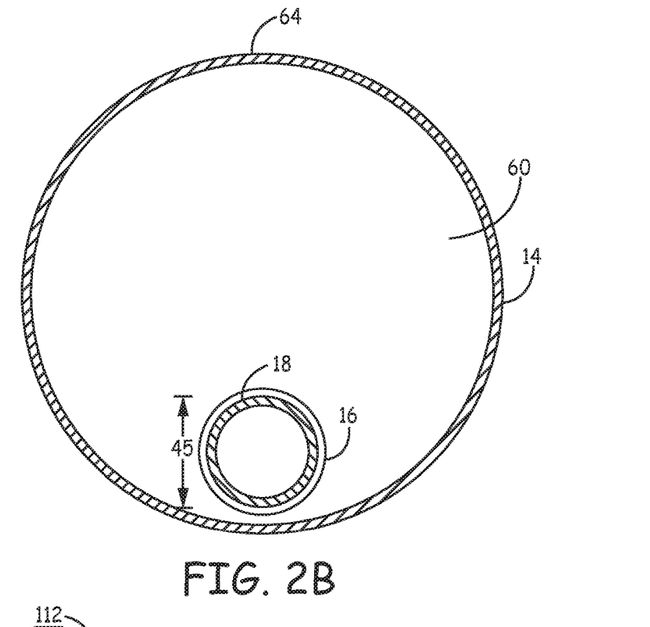

FIG. 2A is side conceptual view and FIG. 2B is a front conceptual view of IMD 12 according to another example. IMD 12 includes hermetically sealed housing 14 including window 16 formed of a high resistivity material such as sapphire or glass. Receiving coil 18 is positioned within housing 12, adjacent window 16. An internal near-field focusing plate 34 is positioned adjacent receiving coil 18. In the example shown, coil 18 is positioned between window 16 and plate 34. Alternately, near-field focusing plate 34 is positioned between window 16 and receiving coil 18.

Housing 14 includes opposing major side walls 60 and 62, referred to herein as "front wall 60" and an opposing "back wall 62," separated by a circumscribing side wall 64. Housing 14 is shown as a circular housing in FIG. 2B, but other prismatic shapes are possible in which case circumscribing side wall 64 defines the two pairs of opposing minor side walls of IMD housing 14 (e.g., top and bottom and left and right minor side walls). Window 16 extends along a portion of front wall 60. In this example, housing 14 includes a second window 36 along back wall 62, opposite window 16, and adjacent to internal near-field focusing plate 34. Internal near-field focusing plate 34 is configured to focus scattered EM energy that radiates beyond coil 18 toward window 36. Window 16 may be referred to as the "receiving window" since transmitted energy is received through window 16, and window 36 may be referred to as the "exiting window" because the EM field 38 is focused to "exit" IMD 12 via window 36 rather than dissipating through other portions of housing 14. When housing 14 is formed of metal, heating caused by the scattered EM energy can pose safety concerns as well as reduce total power transfer efficiency.

Window 16 has an outer dimension, e.g., a length, width or diameter. Near-field focusing plate 34 includes micro- or nano-structures that provide a subwavelength focal pattern that falls within the outer dimension of exiting window 36. Transmission of the re-focused energy field 38 through window 36 for dissipation through body tissue reduces heating of IMD housing 14 during power transfer that might otherwise occur as scattered EM energy dissipates through housing 14. The focusing structures formed on internal near-field focusing plate 34 may be designed to re-focus the EM energy entering the IMD housing 14 along a focal plane 40 that is approximately co-planar with window 36. In other words, the focal length 42 is approximately equal to the distance between the near-field focusing plate 34 and the exiting window 36 such that the EM field 38 extending beyond coil 18 is focused onto window 36. In other examples, the focal length 42 may be greater than the distance between window 36 and internal near-field focusing plate 34 such that a focal plane is exterior to IMD 12. The re-focused energy field 38 that travels beyond window 36 dissipates through surrounding tissue without excessive heating.

In some examples, window 36 is smaller in size (length and width or diameter) than window 16 since the re-focused energy field 38 may be focused to an even smaller focal pattern. The focal pattern produced by internal near-field focusing plate 34 may be a line or spot that falls substantially within the outer dimensions of window 36. In other examples, exiting window 36 is the same size or larger than receiving window 16. The size of exiting window 36 may depend in part on the thickness of the housing material, the thickness of IMD housing 14 relative to the thickness of receiving coil 18. The greater the thickness of IMD housing 14, i.e., the greater the distance from the receiving coil 18 to the opposing side of IMD housing 14, the greater the field divergence may be at the exiting window 36. Near-field focusing plate 34 is configured to focus the EM field to within an exiting window diameter that is equal to or less than the receiving window diameter in some examples.

If the thickness of IMD housing 14 is not significantly greater than the thickness of receiving coil 18, internal near-field focusing plate 34 may not be required since significant divergence of the focused EM field within housing 14 may not occur. In such cases, the internal near-field focusing plate 34 may be eliminated but an exiting window 36 may still be included in housing 14 to minimize losses.

In the front view of FIG. 2B, receiving window 16, coil 18 and internal near-field focusing plate 34 are seen to occupy a relatively small portion of the internal volume of housing 14. Receiving coil 18 may have an overall diameter 45 that is less than or equal to 50% of the overall length 44 of housing 14. Coil 18 may occupy less than a full width and/or thickness of housing 14 in some examples, depending on the overall width and thickness of housing 14. The diameter 45 of receiving coil 18 may be reduced with the use of near-field focusing plate 58 (FIG. 1) at the transmitting coil 56 compared to an implanted coil used in a resonance-type inductive power transfer without near-field focusing. A relatively greater internal volume of housing 14 is available for a hybrid circuit 15, including a rechargeable battery that is charged by coil 18.

Figure 3:
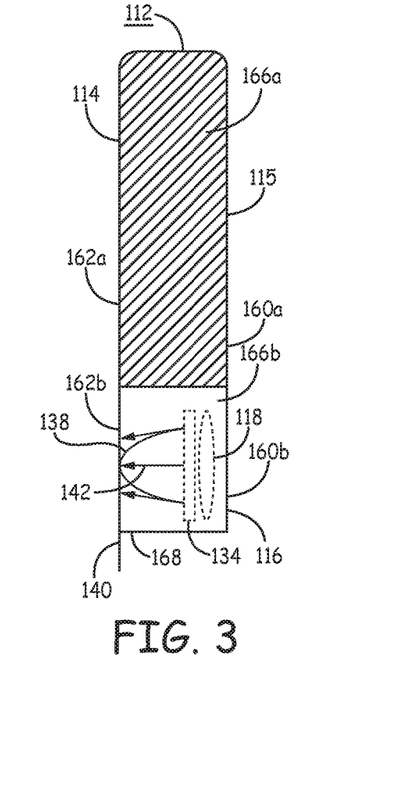
FIG. 3 is a conceptual diagram of an IMD according to another example.

FIG. 3 is a side view conceptual diagram of an IMD 112 according to another example. In FIGS. 2A and 2B, windows 18 and 36 are shown as discrete windows formed along opposing major walls 60 and 62 ("front" and "back") of housing 14. In other examples, as shown in FIG. 3, housing 114 may include an electromagnetically transparent window 116 that circumscribes a portion of housing 114. A first portion 115 of housing 114 may be formed of a metal, e.g., titanium or stainless steel alloys, defining opposing major wall portions 160a and 162a separated by minor side wall portion 166a. Electromagnetically transparent window 116 defines opposing major side portions 160b and 162b and minor side wall portion 166b of housing 112 and may define end wall 168.

Coil 118 is exposed from multiple directions through housing portion 116 for receiving power transmission from transmitting coil 56. Shifting or rotation of IMD 112 within the patient is less likely to cause misalignment of circumferential window 116 with the focused EM field transmitted by transmitting coil 56 than when a discrete window is used, such as window 16. EM energy directed toward the interior of housing 114 is re-focused, as indicated schematically by EM field line 138, toward an opposing side 162b of circumferential window 116 by internal near-field plate 134. The focal length 142 may be approximately equal to or greater than the distance from near-field plate 134 to opposing side 162b.

While IMD 112 is shown having a generally prismatic housing 114, it is contemplated that the techniques disclosed herein may be implemented with a substantially cylindrical housing, having opposing discrete receiving and exiting windows or a circumferential window for passing received EM energy to a receiving coil and re-focused EM energy out of the housing. In other examples, the entirety of housing 112, rather than only a portion, is formed of a magnetically transparent, high resistivity material such as glass, sapphire, ceramic, or polymer material. In this case, the entirety of housing 112 acts as receiving and exiting windows.

Figure 4:
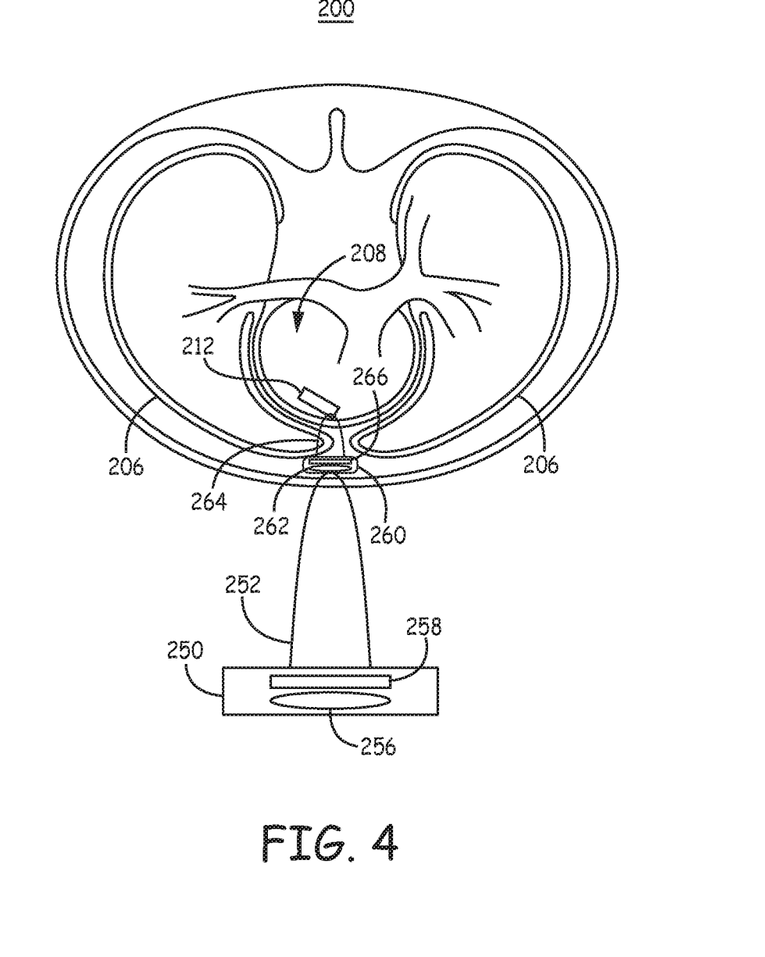
FIG. 4 is a schematic diagram of a system including an IMD and an external charging unit.

FIG. 4 is a schematic diagram of an IMD system 200 including IMD 212 and external charging unit 250. A transverse thoracic view of a patient is shown including heart 208 and lungs 206. In some examples, external charging device 250 may be placed in close proximity to or against the patient's skin, e.g., as shown in FIG. 1, to provide focused near-field power transmission to an IMD, e.g., IMD 12. In other examples, the charging unit 250 may be a distance away from the patient. In the example of FIG. 4, IMD system 200 includes an implantable repeater charging unit 260, including a repeater coil 262 and near-field focusing plate 266. Transmitting coil 256 of external charging unit 250 produces an EM field 252 when a drive signal is applied to coil 256 by a power transfer control module powered by an external power source (not shown in FIG. 4), as described above in conjunction with FIG. 1.

External charging unit 250 may include a near-field focusing plate 258 for subwavelength focusing of EM field 252 as described above. Current induced in repeater coil 262 by EM field 252 produces an EM field 264 that is focused by near-field focusing plate 266 included in repeater charging unit 260. The relative position of repeater charging unit 260 and IMD 212 may be relatively stable such that near-field focusing plate 266 can be designed to focus EM field 264 with a focal length and pattern that is efficiently coupled to the receiving coil (not shown in FIG. 4) enclosed by the housing of IMD 212. In one example, repeater charging unit 260 may be implanted subcutaneously below the xyphoid process or ribcage to direct EM field 264 toward IMD 212. In another example, the repeater charging unit 260 may be implanted substernally.

As described above in conjunction with FIGS. 1-3, the housing of IMD 212 includes an electromagnetically transparent window for passing the focused EM field 264 to an adjacent receiving coil enclosed by the housing of IMD 212. IMD 212 may further include an exiting window and near-field focusing plate to refocus the EM field entering IMD 212 out the exiting window for dispersion by surrounding tissue to minimize heating of the IMD housing.

IMD 212 may be an intracardiac pacemaker in one example, having a miniaturized size for transcatheter implantation in a patient's heart 208, with limited battery space available. EM field 264 may be transmitted to IMD 212 to recharge a rechargeable cell included in IMD 212, thereby extending the functional life of IMD 212. In some examples, the EM field 264 may be used to trigger an operation of IMD 212 in addition to providing power transfer to IMD 212. For example, IMD 212 may be implemented as a passive sensor that is triggered to acquire a physiological signal as long as EM field 264 is present, e.g., a cardiac electrical signal or a pressure signal, and transmit the signal to another implanted or external device (not shown). Examples of triggered implantable medical device systems that may incorporate trigger signal techniques as disclosed herein are generally disclosed in U.S. patent application Ser. No. 14/695,004, Publication No. US 2015-0321011 A1 (Carney et al.), Ser. No. 14/694,990, Publication No. US 2015-0321016 A1 (O'Brien et al.), and Ser. No. 14/695,013, Publication No. US 2015-0321012 A1 (Cinbis et al.), all of which are incorporated herein by reference in their entirety.

IMD 212 may be triggered by EM field 264 to perform a therapy delivery operation, a sensing operation and/or wake-up a telemetry module to perform wireless communication with another device. IMD 212 may start an operation in response to EM field 264 causing a trigger signal to be generated by a power monitoring/regulator as described above. Power required to execute the operation may be provided by a rechargeable battery included by IMD 212 and/or a primary, non-rechargeable battery. In other examples, IMD 212 performs the triggered operation as long as EM field 264 is present.

When the IMD system 200 includes repeater charging unit 260, IMD 212 may be triggered to perform operations (sensing, therapy delivery and/or bidirectional wireless communication) by repeater charging unit 260 when the external charging unit 250 is emitting EM field 252 or not. In some examples, repeater charging unit 260 may include a primary power source and/or a rechargeable power source (that is charged via near-field focused EM field 252). Repeater charging unit 260 may generate EM field 264 as a triggering signal that is "pulsed" for short time intervals to trigger IMD operations without necessarily producing EM field 264 for a long enough time interval to recharge a rechargeable battery of IMD 212. The power for emitting EM field 264 as a trigger signal may be provided by the primary or rechargeable power source of repeater charging unit 260.

In such examples, repeater charging unit 260 may include a sensing module for sensing physiological signals for determining when a therapy is needed and trigger IMD 212 to deliver a therapy, e.g., a therapeutic stimulation pulse, by focusing EM field 264 at a focal length corresponding to a focal plane including a receiving coil positioned adjacent to a receiving window. An exiting window and/or second implanted near-field focusing plate included in IMD 212 may decrease attenuation and minimize energy losses for providing an efficient, low- or zero-power triggered IMD system 200.

In other examples, repeater charging unit may include a telemetry module for bidirectional wireless communication with IMD 212. Near-field focused EM field 264 may be produced to provide a wake-up signal that causes IMD 212 to power-up its telemetry module for establishing a communication session with repeater charging unit 260. Repeater charging unit may receive data from IMD 212 and store the data for later transfer to an external device.

As suggested by the foregoing examples, repeater charging unit 260 may be a dedicated charging device for receiving focused EM field 252 and producing and focusing near-field EM field 264 and, in other examples, repeater charging unit 260 may include other capabilities in addition to power transference. For example, repeater charging unit may include a sensing module, a therapy delivery module and/or a telemetry module and may operate in cooperation with IMD 212 to perform patient monitoring and/or therapy delivery functions.

It is contemplated that IMD 212 and repeater charging unit 260 may be implanted at other locations within the patient's body as required for a particular monitoring and/or therapy delivery application. The examples and techniques disclosed herein for providing efficient power transfer and/or triggered operation by generating a focused pattern of near-field EM energy in an IMD system are not limited to a particular type of IMD system or implant location.

The systems of FIG. 1 or FIG. 4 may be configured to perform a method that includes focusing an EM near field in a focal pattern along a focal plane that includes the receiving coil of the IMD 12 or 212, detecting current induced in the receiving coil by the power monitoring and regulator module 32, and delivering an electrical stimulation pulse by the pulse generator upon detecting the current. A potential developed by the induced current may be coupled directly to the signal generator 24 by the power monitoring and regulator module 32 without the use of a rechargeable cell 30 or other intervening energy storage device. Alternatively, rechargeable cell 30 may be coupled to signal generator 24 to cause generation of an electrical stimulation pulse.

Thus, various examples of a rechargeable IMD system have been described. Aspects disclosed herein may be combined in different combinations than the particular combinations presented in the illustrative embodiments shown in the accompanying drawings. It is recognized that various modifications may be made to the described embodiments without departing from the scope of the following claims.

The invention claimed is:

1. An implantable medical device, comprising:
a housing having a major length, the housing comprising:
a first side comprising a first portion and a second portion, wherein the first portion defines a first window having an outer dimension, the first window comprising an electromagnetically transparent material, wherein the second portion comprises a conductive metal, and wherein the first window outer dimension is less than or equal to half of the housing major length;
a receiving coil enclosed by the housing, the receiving coil extending adjacent to and aligned with the first window; and
a rechargeable cell configured to be charged by the receiving coil when the receiving coil is exposed to a subwavelength focused electromagnetic field that traverses the first window with a focal pattern size that is less than the first window outer dimension.

2. The device of claim 1, further comprising:
a near-field focusing plate adjacent the receiving coil and comprising subwavelength structures for re-focusing electromagnetic energy entering the housing.

3. The device of claim 2, wherein the housing further comprises:
a second side comprising a third portion and a fourth portion, wherein the third portion defines a second window comprising an electromagnetically transparent material, and wherein the fourth portion comprises the conductive metal, the second window extending along the second side in opposition to the first window, the near-field focusing plate configured to re-focus the electromagnetic energy toward the second window.

4. The device of claim 3, wherein:
the second window has an outer dimension; and
the near-field focusing plate comprises subwavelength structures for producing a focal pattern size that is less than the outer dimension of the second window.

5. The device of claim 4, wherein the outer dimension of the second window is less than the outer dimension of the first window.

6. The device of claim 3, wherein:
the near-field focusing plate and the second window are spaced apart by a distance, and
the near-field focusing plate is configured to re-focus the electromagnetic energy entering the housing at a focal length that is at least the distance between the near-field focusing plate and the second window.

7. The device of claim 1, wherein the first window is a discrete window extending along an opening in the second portion.

8. The device of claim 1, further comprising:
a signal generator powered by the rechargeable cell; and
a control module configured to control the signal generator to deliver an electrical stimulation therapy to a patient.

9. The device of claim 1, further comprising:
a sensing module coupled to a physiological sensor for sensing a physiological signal of a patient, the sensing module powered by the rechargeable cell.

10. The device of claim 1, wherein the housing further comprises:
a second side opposite the first side, the second side comprising a third portion and a fourth portion; and
a sidewall separating the first side and the second side,
wherein the third portion defines a second magnetically transparent window, the second window extending along the second side opposite the first window, and wherein the fourth portion comprises the conductive metal,
the receiving coil being between the first window and the second window.

11. The device of claim 1, wherein the receiving coil has an inner diameter that is at least equal to the first window outer dimension.

12. The device of claim 1, further comprising a high impedance load configured to generate a potential signal in response to a current induced in the receiving coil, the potential signal triggering the device to perform a function.

13. The device of claim 12, further comprising at least one of:
a signal generator triggered by the potential signal to deliver a therapeutic stimulation pulse;
a sensing module triggered by the potential signal to acquire a physiological signal; and
a telemetry module triggered by the potential signal to establish a bidirectional communication session with another medical device.

14. The device of claim 13, wherein the trigger signal controls a time at which the function is performed and supplies at least a portion of electrical power required to perform the function.

* * * * *